(12) United States Patent
Bearden

(10) Patent No.: US 11,058,240 B2
(45) Date of Patent: Jul. 13, 2021

(54) PRESSURE MONITOR PILLOW

(71) Applicant: Joshua Bearden, Wasilla, AK (US)

(72) Inventor: Joshua Bearden, Wasilla, AK (US)

( * ) Notice: Subject to any disclaimer, the term of this patent is extended or adjusted under 35 U.S.C. 154(b) by 62 days.

(21) Appl. No.: 16/539,591

(22) Filed: Aug. 13, 2019

(65) Prior Publication Data

US 2021/0045552 A1 Feb. 18, 2021

(51) Int. Cl.
| | |
|---|---|
| *A47G 9/10* | (2006.01) |
| *A47C 27/08* | (2006.01) |
| *A47G 9/02* | (2006.01) |
| *A61G 13/12* | (2006.01) |

(52) U.S. Cl.
CPC .......... *A47G 9/1027* (2013.01); *A47C 27/083* (2013.01); *A47G 9/0253* (2013.01); *A61G 13/12* (2013.01)

(58) Field of Classification Search
CPC ...... A47G 9/10; A47G 9/1027; A47G 9/0253; A47G 9/1045; A47G 2009/1018; A47C 27/083; A61G 13/12; A61G 13/121
See application file for complete search history.

(56) References Cited

U.S. PATENT DOCUMENTS

| | | | | |
|---|---|---|---|---|
| 6,081,949 | A * | 7/2000 | Delicia | G04G 13/021 368/12 |
| 7,461,422 | B1 * | 12/2008 | Baker | G04B 47/02 5/639 |
| 9,775,443 | B2 | 10/2017 | Spahn | |
| 2005/0165284 | A1 | 7/2005 | Gefen | |
| 2011/0296622 | A1 * | 12/2011 | Hsu | A47C 27/083 5/713 |
| 2012/0065547 | A1 | 3/2012 | Hann | |
| 2013/0281804 | A1 | 10/2013 | Lee | |
| 2014/0039351 | A1 | 2/2014 | Mix | |
| 2014/0130261 | A1 * | 5/2014 | Gumbrecht | A47C 7/383 5/644 |
| 2014/0345058 | A1 * | 11/2014 | Escobedo | A61G 5/1045 5/655.3 |
| 2017/0027792 | A1 | 2/2017 | Laffeche | |
| 2017/0127858 | A1 * | 5/2017 | Teh | A47G 9/1045 |

FOREIGN PATENT DOCUMENTS

WO WO2012122002 9/2012

* cited by examiner

*Primary Examiner* — Robert G Santos
*Assistant Examiner* — Rahib T Zaman

(57) ABSTRACT

A pressure monitor pillow for preventing pressure injuries includes a pillow body configured to fit within a standard pillow case. A plurality of pressure sensors is coupled to a top side of the pillow body. A control housing is coupled to the pillow body and has a battery compartment with a removable. A logic board is coupled within the control housing and is in operational communication with each of the plurality of pressure sensors and the battery compartment. A display screen is coupled to the control housing and is in operational communication with the logic board and the battery compartment. The display screen shows a pressure reading from the plurality of pressure sensors. A power button is coupled to the control housing and is in operational communication with the logic board and the battery compartment.

9 Claims, 5 Drawing Sheets

PRESSURE MONITOR PILLOW

CROSS-REFERENCE TO RELATED APPLICATIONS

Not Applicable

STATEMENT REGARDING FEDERALLY SPONSORED RESEARCH OR DEVELOPMENT

Not Applicable

THE NAMES OF THE PARTIES TO A JOINT RESEARCH AGREEMENT

Not Applicable

INCORPORATION-BY-REFERENCE OF MATERIAL SUBMITTED ON A COMPACT DISC OR AS A TEXT FILE VIA THE OFFICE ELECTRONIC FILING SYSTEM

Not Applicable

STATEMENT REGARDING PRIOR DISCLOSURES BY THE INVENTOR OR JOINT INVENTOR

Not Applicable

BACKGROUND OF THE INVENTION

(1) Field of the Invention

(2) Description of Related Art Including Information Disclosed Under 37 CFR 1.97 and 1.98

The disclosure and prior art relates to pillows and more particularly pertains to a new pillow for preventing pressure injuries.

BRIEF SUMMARY OF THE INVENTION

An embodiment of the disclosure meets the needs presented above by generally comprising a pillow body having a top side, a bottom side, a left side, a right side, a front side, and a back side. The pillow body is configured to fit within a standard pillow case. A plurality of pressure sensors is coupled to the top side of the pillow body. A control housing is coupled to the pillow body and has a battery compartment. The battery compartment has a removable cover and is configured to receive a plurality of batteries. A logic board is coupled within the control housing and is in operational communication with each of the plurality of pressure sensors and the battery compartment. A display screen is coupled to the control housing and is in operational communication with the logic board and the battery compartment. The display screen shows a pressure reading from the plurality of pressure sensors. A power button is coupled to the control housing and is in operational communication with the logic board and the battery compartment.

There has thus been outlined, rather broadly, the more important features of the disclosure in order that the detailed description thereof that follows may be better understood, and in order that the present contribution to the art may be better appreciated. There are additional features of the disclosure that will be described hereinafter and which will form the subject matter of the claims appended hereto.

The objects of the disclosure, along with the various features of novelty which characterize the disclosure, are pointed out with particularity in the claims annexed to and forming a part of this disclosure.

BRIEF DESCRIPTION OF SEVERAL VIEWS OF THE DRAWING(S)

The disclosure will be better understood and objects other than those set forth above will become apparent when consideration is given to the following detailed description thereof. Such description makes reference to the annexed drawings wherein.

DETAILED DESCRIPTION OF THE INVENTION

Figure 1:
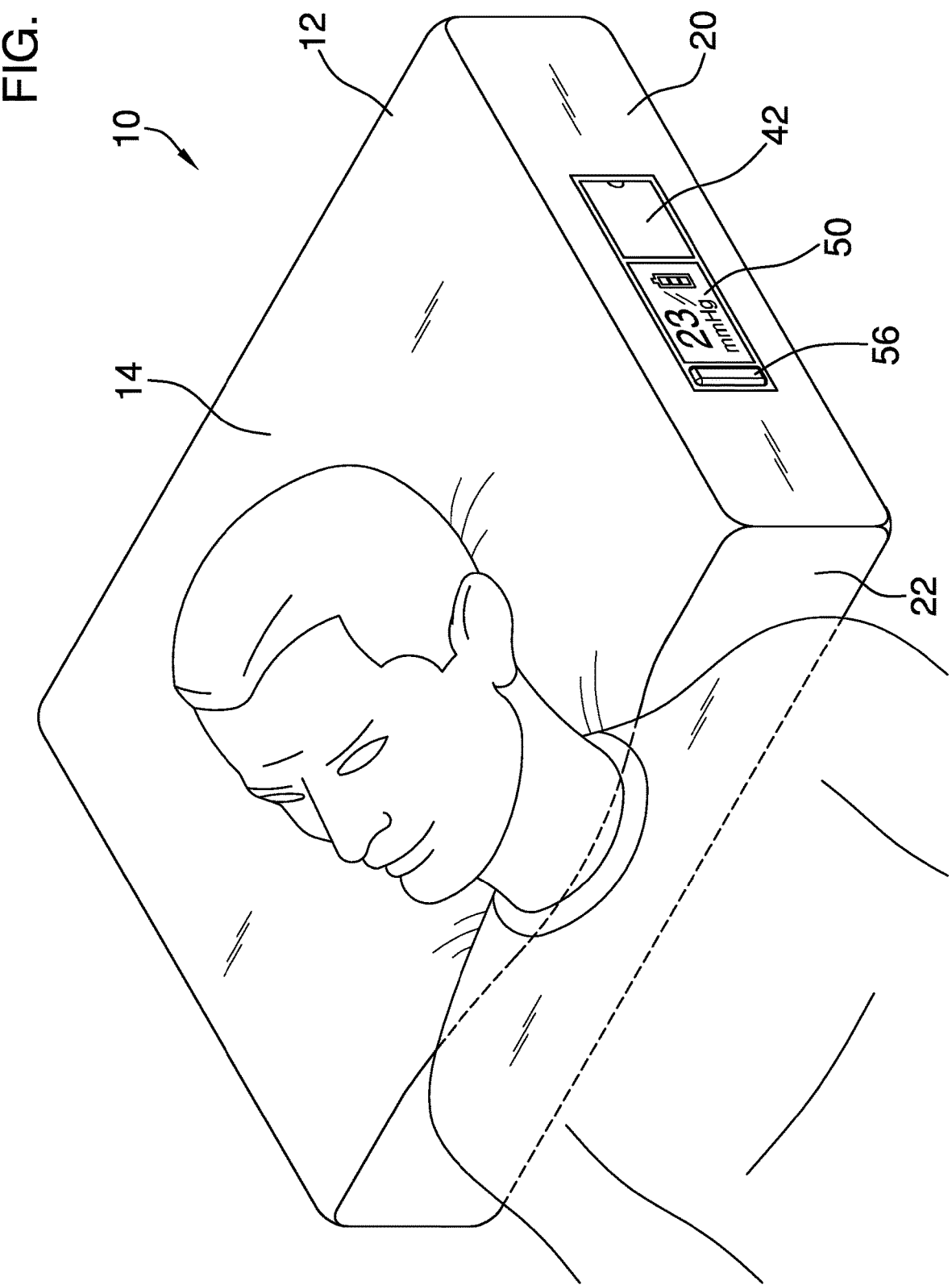
FIG. 1 is an isometric view of a pressure monitor pillow according to an embodiment of the disclosure.
Figure 2:
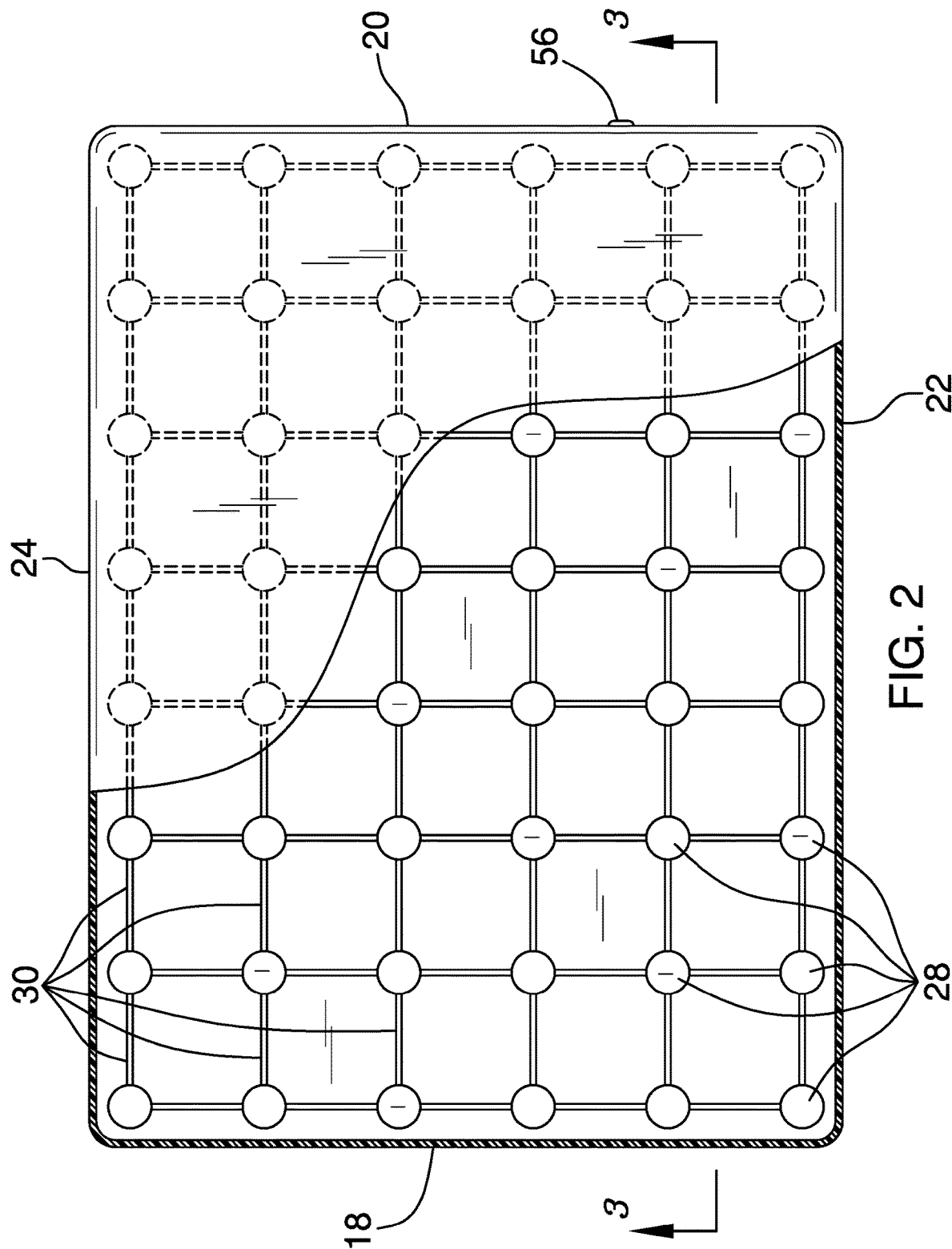
FIG. 2 is a top plan view of an embodiment of the disclosure.
Figure 3:
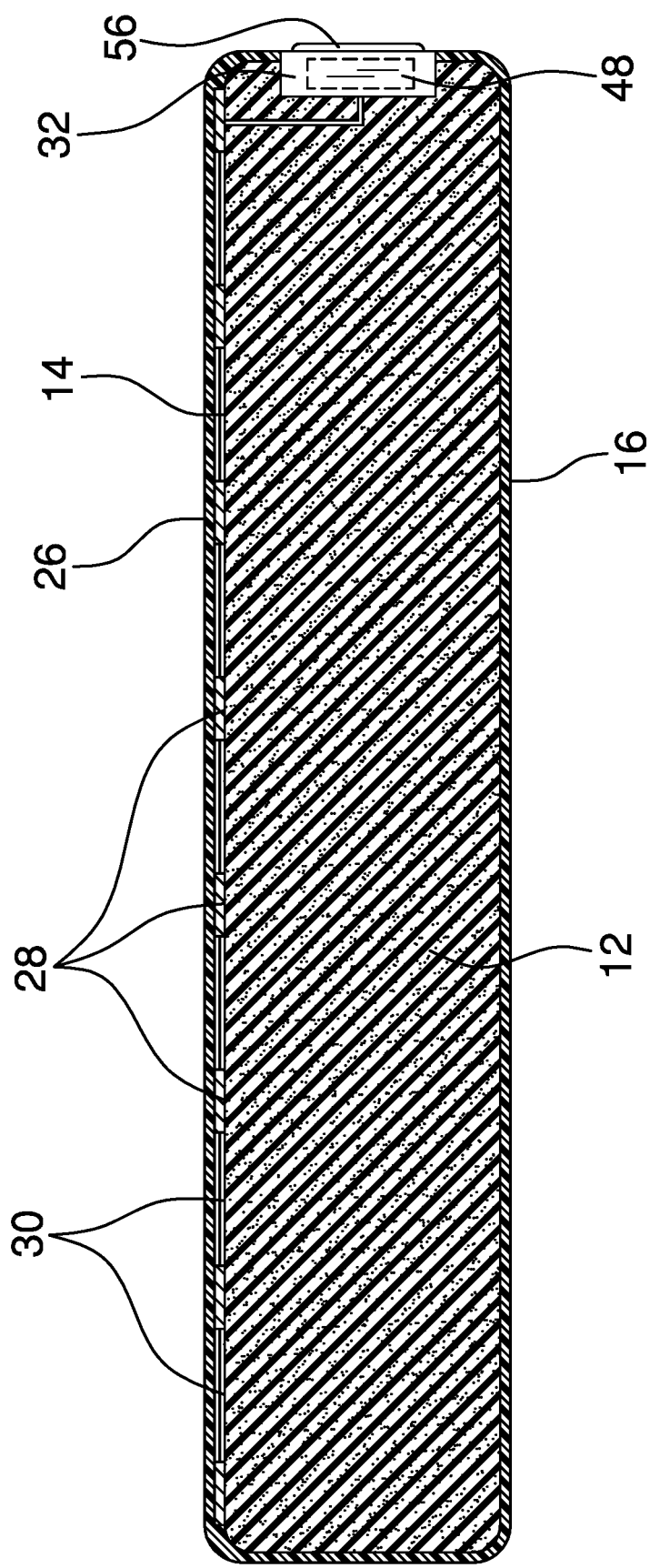
FIG. 3 is a cross-sectional view of an embodiment of the disclosure along line 3-3 of FIG. 2.
Figure 4:
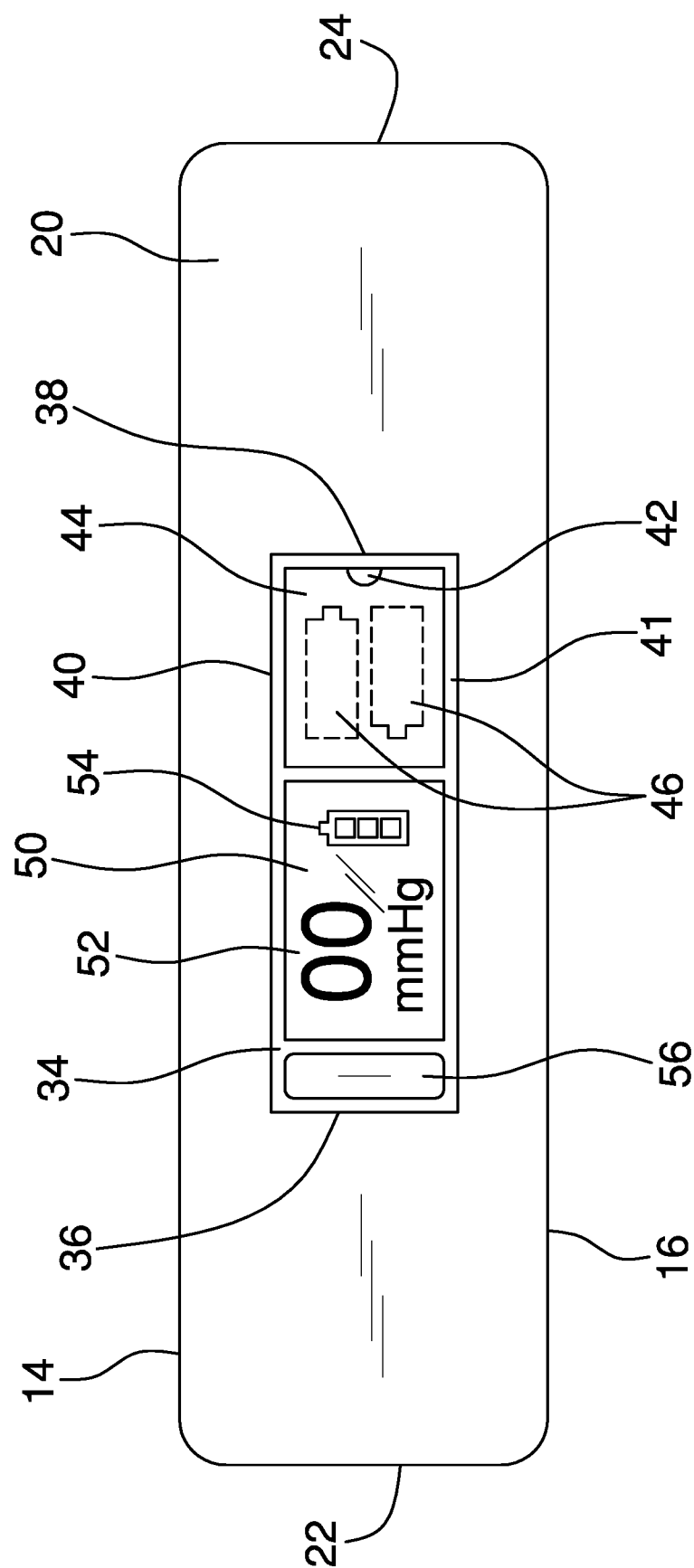
FIG. 4 is a side elevation view of an embodiment of the disclosure.
Figure 5:
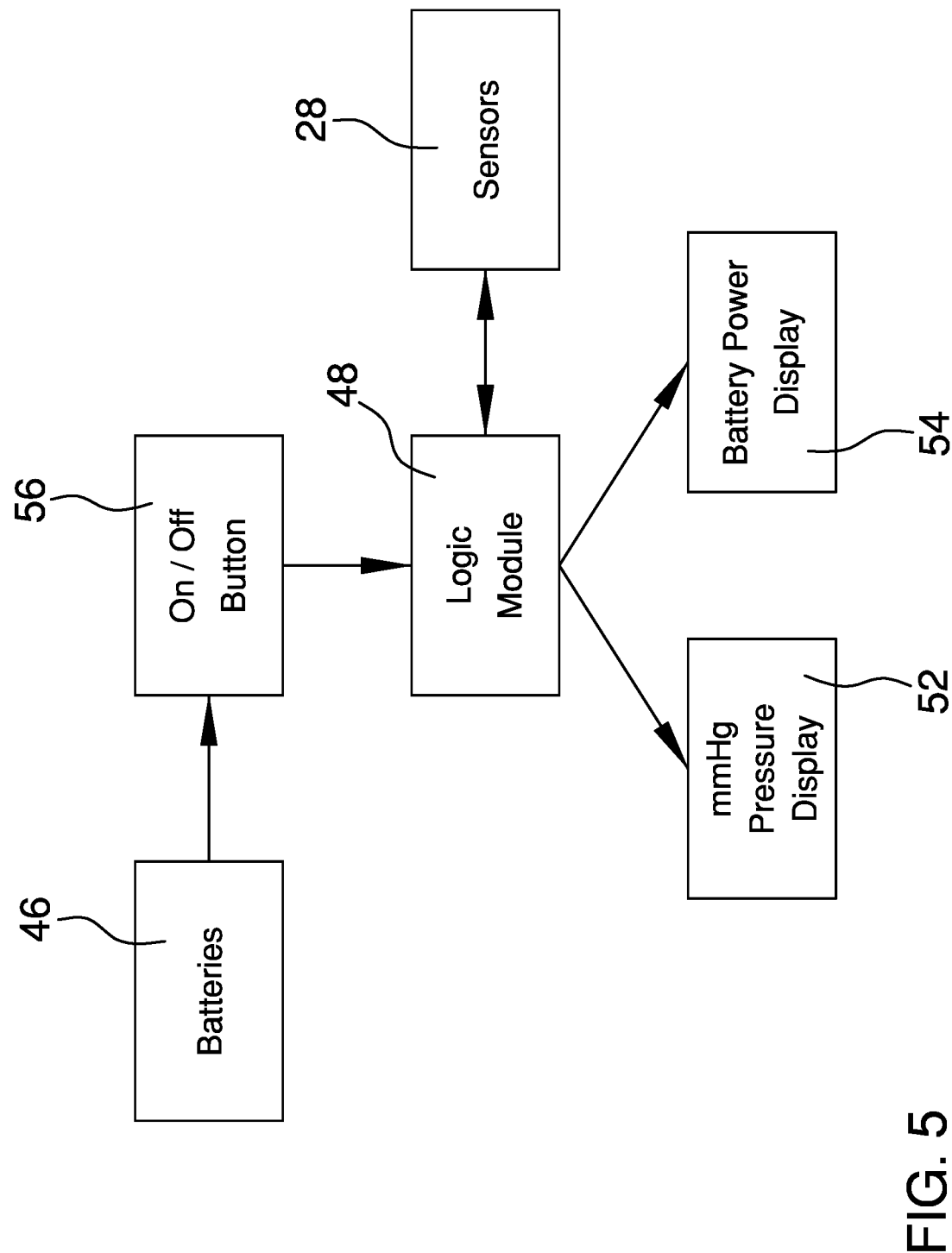
FIG. 5 is a block diagram of an embodiment of the disclosure.

With reference now to the drawings, and in particular to FIGS. 1 through 5 thereof, a new pillow embodying the principles and concepts of an embodiment of the disclosure and generally designated by the reference numeral 10 will be described.

As best illustrated in FIGS. 1 through 5, the pressure monitor pillow 10 generally comprises a pillow body 12 having a top side 14, a bottom side 16, a left side 18, a right side 20, a front side 22, and a back side 24. The pillow body 12 is configured to fit within a standard pillow case. A cover layer 26 may be continuously coupled to each of the top side 14, the bottom side 16, the left side 18, the right side 20, the front side 22, and the back side 24. The cover layer may be waterproof.

A plurality of pressure sensors 28 is coupled to the pillow body 12. The plurality of pressure sensors 28 is coupled to the top side 14 beneath the cover layer 26. The plurality of pressure sensors 28 may be arranged in a matrix and is interconnected by a plurality of wires 30. A control housing 32 is coupled to the pillow body 12. The control housing 32 may have a frame 34 disposed flush with the right side 20 of the pillow body. The frame 34 has a front edge 36, a back edge 38, a top edge 40, and a bottom edge 41. The control housing 32 has a battery compartment 42 with a removable cover 44 disposed flush with the frame 34 adjacent the back edge 38. The battery compartment 42 is configured to receive a plurality of batteries 46. The control housing 32 is coupled through the cover layer 26. A logic board 48 is coupled within the control housing 12 and is in operational communication with each of the plurality of pressure sensors 28 and the battery compartment 42.

A display screen 50 is coupled to the control housing 32 flush with the frame 34 and adjacent the battery compartment 42. The display screen 50 is in operational communication with the logic board 48 and the battery compartment 42. The display screen 50 may comprise a pressure display 52 and a battery power display 54. The pressure display 52 shows a pressure reading, which may be in mmHg, from the plurality of pressure sensors 28. The battery power display 54 shows a battery charge level of the plurality of batteries 46 held within the battery compartment 42. A power button 56 is coupled to the control housing 32 and is in operational communication with the logic board 48 and the battery compartment 42. The power button 56 extends slightly from the frame 34 adjacent the front edge 36.

In use, the power button 56 is pressed to activate the logic board 48 and the display screen 50. When the pillow body 12 is rested upon, the pressure display 52 will show the amount of pressure being applied to the pressure monitor pillow 10 in order to prevent pressure injuries.

With respect to the above description then, it is to be realized that the optimum dimensional relationships for the parts of an embodiment enabled by the disclosure, to include variations in size, materials, shape, form, function and manner of operation, assembly and use, are deemed readily apparent and obvious to one skilled in the art, and all equivalent relationships to those illustrated in the drawings and described in the specification are intended to be encompassed by an embodiment of the disclosure.

Therefore, the foregoing is considered as illustrative only of the principles of the disclosure. Further, since numerous modifications and changes will readily occur to those skilled in the art, it is not desired to limit the disclosure to the exact construction and operation shown and described, and accordingly, all suitable modifications and equivalents may be resorted to, falling within the scope of the disclosure. In this patent document, the word "comprising" is used in its non-limiting sense to mean that items following the word are included, but items not specifically mentioned are not excluded. A reference to an element by the indefinite article "a" does not exclude the possibility that more than one of the element is present, unless the context clearly requires that there be only one of the elements.

I claim:

1. A pressure monitor pillow comprising:
   a pillow body, the pillow body having a top side, a bottom side, a left side, a right side, a front side, and a back side, the pillow body being configured to fit within a standard pillow case;
   a plurality of pressure sensors coupled to the pillow body, the plurality of pressure sensors being coupled to the top side;
   a control housing coupled to the pillow body, the control housing having a battery compartment, the battery compartment having a removable cover, the battery compartment being configured to receive a plurality of batteries, the control housing having a frame, the frame being disposed flush with the pillow body;
   a logic board coupled to the control housing, the logic board being coupled within the control housing, the logic board being in operational communication with each of the plurality of pressure sensors and the battery compartment;
   a display screen coupled to the control housing, the display screen being in operational communication with the logic board and the battery compartment, the display screen showing a pressure reading from the plurality of pressure sensors, each of the removable cover of the battery compartment and the display screen being flush with the frame; and
   a power button coupled to the control housing, the power button being in operational communication with the logic board and the battery compartment, the power button extending slightly from the frame.

2. The pressure monitor pillow of claim 1 further comprising a cover layer coupled to the pillow body, the cover layer being continuously coupled to each of the top side, the bottom side, the left side, the right side, the front side, and the back side, the control housing being coupled through the cover layer.

3. The pressure monitor pillow of claim 2 further comprising the cover layer being waterproof.

4. The pressure monitor pillow of claim 1 further comprising the plurality of pressure sensors being arranged in a matrix, the plurality of pressure sensors being interconnected by a plurality of wires.

5. The pressure monitor pillow of claim 1 further comprising the display screen comprising a pressure display and a battery power display.

6. The pressure monitor pillow of claim 1 further comprising the pressure display showing in mmHg.

7. The pressure monitor pillow of claim 1 further comprising the frame having a front edge, a back edge, a top edge, and a bottom edge, the power button being disposed adjacent the front edge, the battery compartment being disposed adjacent the back edge, the display screen being disposed between the power button and the battery compartment.

8. A pressure monitor pillow comprising:
   a pillow body, the pillow body having a top side, a bottom side, a left side, a right side, a front side, and a back side, the pillow body being configured to fit within a standard pillow case;
   a plurality of pressure sensors coupled to the pillow body, the plurality of pressure sensors being coupled to the top side;
   a control housing coupled to the pillow body, the control housing having a battery compartment, the battery compartment having a removable cover, the battery compartment being configured to receive a plurality of batteries, the control housing being coupled to the right side of the pillow body;
   a logic board coupled to the control housing, the logic board being coupled within the control housing, the logic board being in operational communication with each of the plurality of pressure sensors and the battery compartment;
   a display screen coupled to the control housing, the display screen being in operational communication with the logic board and the battery compartment, the display screen showing a pressure reading from the plurality of pressure sensors; and
   a power button coupled to the control housing, the power button being in operational communication with the logic board and the battery compartment.

9. A pressure monitor pillow comprising:
   a pillow body, the pillow body having a top side, a bottom side, a left side, a right side, a front side, and a back side, the pillow body being configured to fit within a standard pillow case;
   a cover layer coupled to the pillow body, the cover layer being continuously coupled to each of the top side, the bottom side, the left side, the right side, the front side, and the back side, the cover layer being waterproof;
   a plurality of pressure sensors coupled to the pillow body, the plurality of pressure sensors being coupled to the top side beneath the cover layer, the plurality of pressure sensors being arranged in a matrix, the plurality of pressure sensors being interconnected by a plurality of wires;

a control housing coupled to the pillow body, the control housing having a frame disposed flush with the pillow body, the frame having a front edge, a back edge, a top edge, and a bottom edge, the control housing having a battery compartment, the battery compartment having a removable cover disposed flush with the frame adjacent the back edge, the battery compartment being configured to receive a plurality of batteries, the control housing being coupled through the cover layer;

a logic board coupled to the control housing, the logic board being coupled within the control housing, the logic board being in operational communication with each of the plurality of pressure sensors and the battery compartment;

a display screen coupled to the control housing, the display screen being flush with the frame adjacent the battery compartment, the display screen being in operational communication with the logic board and the battery compartment, the display screen comprising a pressure display and a battery power display, the pressure display showing a pressure reading in mmHg from the plurality of pressure sensors, the battery power display showing a battery charge level; and a power button coupled to the control housing, the power button being in operational communication with the logic board and the battery compartment, the power button extending slightly from the frame adjacent the front edge.

* * * * *